US006369039B1

(12) United States Patent
Palasis et al.

(10) Patent No.: US 6,369,039 B1
(45) Date of Patent: Apr. 9, 2002

(54) HIGH EFFICIENCY LOCAL DRUG DELIVERY

(75) Inventors: Maria Palasis, Wellesley; Kenneth Walsh, Carlisle, both of MA (US)

(73) Assignee: Scimed Life Sytems, Inc., Maple Grove, MN (US)

( * ) Notice: Subject to any disclaimer, the term of this patent is extended or adjusted under 35 U.S.C. 154(b) by 0 days.

(21) Appl. No.: 09/204,254

(22) Filed: Dec. 3, 1998

Related U.S. Application Data

(63) Continuation-in-part of application No. 09/106,855, filed on Jun. 30, 1998, now abandoned.

(51) Int. Cl.[7] .............................................. A61K 48/00
(52) U.S. Cl. ........................... 514/44; 514/2; 424/93.2; 604/51; 604/52; 604/53
(58) Field of Search ............................ 514/44, 449, 411, 514/1, 2, 84; 604/265; 424/93.2; 435/320.1, 455

(56) References Cited

U.S. PATENT DOCUMENTS

| | | | | |
|---|---|---|---|---|
| 4,487,808 A | * | 12/1984 | Lambert ................... | 428/423.1 |
| 5,041,107 A | * | 8/1991 | Heil, Jr. .................... | 604/891.1 |
| 5,061,237 A | * | 10/1991 | Gessler et al. ................. | 604/5 |
| 5,102,402 A | | 4/1992 | Dror et al. ................... | 604/265 |
| 5,103,817 A | * | 4/1992 | Reisdorf et al. ........ | 128/207.15 |
| 5,380,299 A | | 1/1995 | Fearnot et al. .............. | 604/265 |
| 5,383,928 A | | 1/1995 | Scott et al. ..................... | 623/1 |
| 5,464,395 A | | 11/1995 | Faxon et al. ................... | 604/96 |
| 5,599,294 A | | 2/1997 | Edwards et al. .............. | 604/22 |
| 5,624,411 A | | 4/1997 | Tuch .......................... | 604/265 |
| 5,652,225 A | * | 7/1997 | Isner ........................... | 514/44 |
| 5,674,192 A | * | 10/1997 | Sahatjian et al. ............. | 604/28 |
| 5,733,925 A | | 3/1998 | Kunz et al. ................. | 514/449 |
| 5,763,416 A | * | 6/1998 | Bonadio ....................... | 514/44 |
| 5,800,525 A | | 9/1998 | Bachinski et al. ............. | 623/1 |
| 5,846,225 A | | 12/1998 | Rosengart et al. .......... | 604/115 |
| 5,981,568 A | * | 11/1999 | Kunz .......................... | 514/411 |
| 6,228,845 B1 | * | 5/2001 | Donovan et al. ............. | 514/44 |
| 6,251,886 B1 | * | 6/2001 | Friedman .................... | 514/183 |
| 6,273,913 B1 | * | 8/2001 | Wright et al. .............. | 623/1.42 |

FOREIGN PATENT DOCUMENTS

| | | |
|---|---|---|
| EP | 0 372 088 A1 | 2/1989 |
| EP | 0 364 787 | 4/1990 |
| GB | 2 127 839 A | 9/1983 |
| GB | 2 153 235 | 8/1985 |
| WO | WO92/11896 | 7/1992 |
| WO | WO97/41916 | 11/1997 |
| WO | WO98/35784 | 8/1998 |

OTHER PUBLICATIONS

Anderson et al., Nature, vol. 392, 25–30, 1998.*
Verma et al. (Nature, vol. 389, 18, pp. 239–242, 1997.*
Branch (TIBS 23, pp. 45–50), 1998.*
Alain Tedgui and M. John Lever, American Journal of Physiology, Effect of pressure and intimal damage on[131] I–albumin and [$^{14}$C] sucrose spaces in aorta,Dec. 1987, vol. 253/No. 6, 1530–1539.
Tahlil, Ouafae et al.,Cardiovascular Research, The Dispatch catheter as a delivery tool for arterial gene transfer,Jan. 1997, vol. 33, No. 1,181–187.
Schulick, Andrew H., MD, et al.,Circulation, In Vivo Gene Transfer Into Injured Carotid Arteries, vol. 91, No. 9, May 1, 1995,2407–2414.
Feldman, Laurent J. et al. Cardiovascular Research, Optimal techniques for arterial gene transfer, 1997, Research 35, 391–404.
Vassalli, Giuseppe and Dichek, David A., Cardiovascular Research, Gene therapy for arterial thrombosis, 1997, Research 35, 459–469.
Gerard, Robert D. and Collen, Desire, Cardiovascular Research, Adenovirus gene therapy for hypercholesterolemia, thrombosis and restenosis, 1997, Research 35, 451–458.
Steg, P. Gavriel, MD, et al.,Circulation, Arterial Gene Transfer to Rabbit Endothelial and Smooth Muscle Cells Using Percutaneous Delivery of an Adenoviral Vector, Oct. 1994, Vol. 90, No. 4,1648–1656.
Willard, John E., MD, et al., Circulation, Genetic Modification of Vessel Wall, May 1994, vol. 89, No. 5, 2190–2197.
Ohno, Taskeshi, et al., Science, Gene Therapy for Vascular Smooth Muscle Cell Proliferation After Arterial Injury, Aug. 1994, vol. 265, 781–784.
Asahara, Takayuki, MD, et al., Circulation, Local Delivery of Vascular Endothelial Growth Factor Accelerates Reendothelialization and Attenuates Intimal Hyperplasia in Balloon–Injured Rat Carotid Artery, Jun. 1, 1995, vol. 91, No. 11, 2793–2801.
Tedgui, Alain and Lever, M. John, Circulation Research, The Interaction of Convection and Diffusion in the Transport of [131] I–Albumin within the Media of the Rabbit Thoracic Aorta, Dec. 1985, vol. 57, No. 6, 856–863.
Moura, Alvaro, MD, et al., Circulation, Intramural Delivery of Agent via a Novel Drug–Delivery Sleeve, Oct. 15, 1995, vol. 92, No. 8, 2299–2305.

(List continued on next page.)

Primary Examiner—Dave T. Nguyen
(74) Attorney, Agent, or Firm—Kenyon & Kenyon

(57) ABSTRACT

A method of site-specifically delivering a therapeutic agent to a target location within a body cavity, vasculature or tissue. The method comprises the steps of providing a medical device having a substantially saturated solution of therapeutic agent associated therewith; introducing the medical device into the body cavity, vasculature or tissue; releasing a volume of the solution of therapeutic agent from the medical device at the target location at a pressure of from about 0 to about 5 atmospheres for a time of up to about 5 minutes; and withdrawing the medical device from the body cavity, vasculature or tissue. In another aspect, the present invention includes a system for delivering a therapeutic agent to a body cavity, vasculature or tissue, comprising a medical device having a substantially saturated solution of the therapeutic agent associated therewith.

19 Claims, 2 Drawing Sheets

OTHER PUBLICATIONS

Lewis, Basil S., et al., Cardiovascular Research, Angiogenesis by gene therapy: a new horizon for myocardial revascularization?, Sep. 1997, vol. 35, No. 3, 490–497.

Swain, Judith L., MD, Circulation, GENE THERAPY A New Approach to the Treatment of Cardiovascular Disease, Nov. 1989, vol. 80, No. 5, 1495–1496.

American Heart Association, Supplemental to Circulation, Oct. 15, 1995, vol. 92, No. 8, 670–672.

Axel, Dorothea I., et al., Paclitaxel Inhibits Arterial Smooth Muscle Cell Proliferation and Migration In Vitro and In Vivo and In Vivo Using Local Drug Delivery, Jul. 15, 1997, 636–651.

Gehrke, S.H., et al., "Enhanced loading and activity retention of bioactive proteins in hydrogel delivery systems," Journal of Controlled Release 55 (1998) pp. 21–33.

* cited by examiner

HIGH EFFICIENCY LOCAL DRUG DELIVERY

The present application is a continuation-in-part of application Ser. No. 09/106,855, filed Jun. 30, 1998, abandoned.

FIELD OF THE INVENTION

The present invention relates to the site-specific delivery of therapeutic agents to target locations within body cavities, vasculatures, or tissues.

BACKGROUND

The treatment of disease such as vascular disease by local pharmacotherapy presents a means of delivering therapeutic drug doses to target tissues while minimizing systemic side effects. Recently, for example, the local delivery of gene constructs to effect vascular response has gained increased interest. Gene transfection of vascular smooth muscle cells in vivo, however, remains a problem due to low transfer efficiency attributed in part to inefficient local delivery devices and to the barrier properties of the vessel wall.

As an example of localized delivery of therapeutic agents, in vivo adenoviral gene transfer has been accomplished with the use of site-specific delivery catheters. Independent of the local delivery device used, most studies have delivered viral doses ranging from $1\times10^9$ to $1\times10^{10}$ pfu/ml over extended delivery times of 20 minutes or longer, and typically in delivery volumes of 1 ml or more. Although these conditions are widely used, the lack of optimization studies with local delivery devices suggests that delivery conditions are not necessarily optimal. Moreover, conventional localized techniques are often invasive in that they typically involve side branch ligation, long delivery times, and when the delivery device is an expandable device such as a balloon catheter, these techniques usually are associated with high pressures to accomplish drug delivery. Localized delivery techniques making use of long delivery times and high pressures and volumes often result in tissue damage, ischemia and other problems. Attempts have been made to reduce the delivery time from an infusion based device using a polymer carrier such as Poloxamer (BASF Corporation), whereby delivery times are reduced from 30 minutes to 5 minutes. The clinical utility of this approach, however, remains uncertain.

SUMMARY OF THE INVENTION

In one aspect, the present invention includes a method of site-specifically delivering a therapeutic agent to a target location within a body cavity, vasculature or tissue. The method comprises the steps of providing a medical device having a substantially saturated solution of therapeutic agent associated therewith; introducing the medical device into the body cavity, vasculature or tissue; releasing a volume of the solution of therapeutic agent from the medical device at the target location at a pressure of from about 0 to about 5 atmospheres for a time of up to about 5 minutes; and withdrawing the medical device from the body cavity, vasculature or tissue.

In another aspect, the present invention includes a system for delivering a therapeutic agent to a body cavity, vasculature or tissue, comprising a medical device having a substantially saturated solution of the therapeutic agent associated therewith.

DETAILED DESCRIPTION

Figure 1:
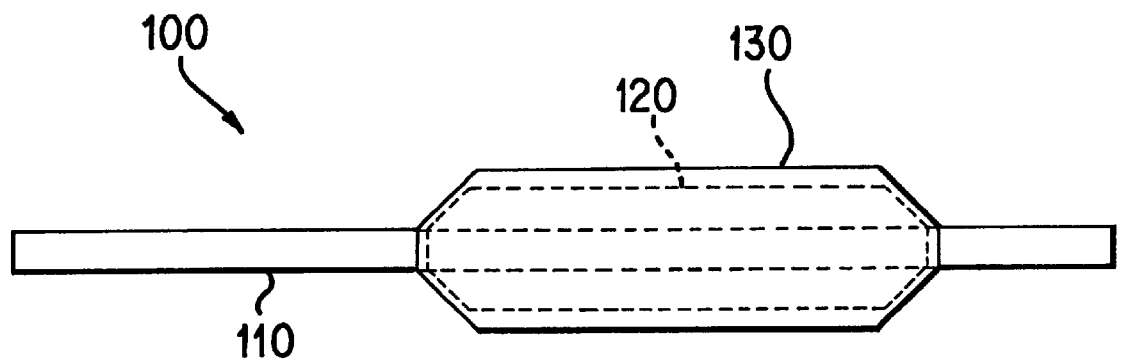
FIG. 1 shows a medical device in accordance with an embodiment of the present invention.

The present invention overcomes the deficiencies of conventional localized drug delivery techniques by providing a site-specific, minimally-invasive method of delivering therapeutic agents to tissue. The method of the present invention advantageously makes use of low delivery pressures and short delivery durations to provide for the quick and safe localized delivery of therapeutic agents to any suitable lumen, cavity, or tissue in the body such as, for example, blood vessels, heart tissue, and locations within the gastrointestinal tract and urological and gynecological systems. The terms "drug" and "therapeutic agent" are used interchangeably herein and include pharmaceutically active compounds, nucleic acids with and without carrier vectors such as lipids, compacting agents (such as histones), virus, polymers, proteins, and the like, with or without targeting sequences.

In the localized delivery of therapeutic agents, pressure-driven convection and concentration-driven diffusion are the two predominant transport mechanisms in the target tissue. The relative importance of these mechanisms, however, has previously not been well-understood. Convective flow is defined as fluid flow through a solvent space due to a pressure difference acting across a region of tissue. Convective solute transport occurs when dissolved solutes are carried along with the fluid flow. Although small molecules are generally easily convected with the fluid flow, a sieving effect by the tissue tends to retard large molecules. In contrast to convective transport, molecular diffusion is defined as solute transport from regions of high concentration to regions of low concentration due to random molecular motions. Transport due to molecular diffusion is directly proportional to an applied concentration gradient.

The inventors have surprisingly discovered that under appropriate conditions, therapeutic agents are transported into tissue in a manner consistent with molecular diffusion. Correspondingly, the inventors have surprisingly found that variations in applied pressure during localized drug administration has no significant effect on the transport of drug agents or other therapeutic agents into target tissue. The present invention makes use of this finding by providing for drug delivery based on the principles of concentration-driven diffusion. Delivery of therapeutic agents is thus achieved by controlling the concentration of therapeutic agent at a target location, rather than relying on pressure-driven processes.

In one aspect, the present invention includes a method of site-specifically delivering a therapeutic agent to a target location within a body cavity, vasculature or tissue of a mammal. The method comprises the steps of providing a medical device having a substantially saturated solution of therapeutic agent associated therewith; introducing the medical device into the body cavity, vasculature, or tissue sought to be treated; releasing the solution of therapeutic agent from the medical device at the target location at a pressure of from about 0 to about 5 atmospheres; and withdrawing the medical device from the target location within about 5 minutes from the time of releasing the solution from the medical device.

To achieve high efficiency drug delivery by concentration-driven molecular diffusion, the therapeutic agent is incorporated into the medical device as a substantially saturated solution. As used herein, "substantially saturated solution" means that the concentration of dissolved therapeutic agent in a solvent, such as water or another physiologically acceptable carrier, is at least about 75%, preferably at least about 80%, 85%, 90%, 95% or 100% of the limit of solubility of the therapeutic agent in the solvent. Alternatively, the concentration of the therapeutic agent is limited by the concentration that results in an undesirable toxic response from a patient. The substantially saturated solution is "associated with" the medical device in that the therapeutic agent is held in a cavity(ies) of the device, such as in an infusion style catheter such as a channel balloon catheter; or the therapeutic agent is coated onto the surface of the device as a coating per se or as part of a coating; or the substantially saturated solution is held within or passes through the medical device, such as in a needle injection catheter.

The present invention is described herein with specific reference to an expandable catheter as the medical device. Other medical devices within the scope of the present invention include implantable devices such as needle injection catheters, hypodermic needles, stents, blood clot filters, vascular grafts, stent grafts, aneurysm filling coils, trans myocardial revascularization ("TMR") devices, percutaneous myocardial revascularization ("PMR") devices etc., as are known in the art.

The catheter used with the present invention is any suitable catheter such as, for example, an infusion catheter (such as a channeled balloon catheter as described in U.S. Pat. No. 5,254,089, incorporated herein by reference, transport catheter, or microporous balloon catheter), an angioplasty balloon catheter, a double balloon catheter, or an infusing sleeve catheter, as are known in the art. The therapeutic agent is applied to, or is incorporated into, the expandable portion of such catheters. For example, the therapeutic agent is included as part of a polymer coating that is applied to said expandable portions. Alternatively, the therapeutic agent is incorporated directly into the expandable portion. Alternatively, the therapeutic agent is introduced into the catheter after the catheter is positioned to the target tissue by infusing the therapeutic agent through the infusion port of an-infusion catheter.

In accordance with the present invention, once the catheter is positioned at the target location, the therapeutic agent is released at a pressure of not more than about 5 atmospheres, preferably not more than about 1 atmosphere, and more preferably, not more than about 0.1 atmosphere. The catheter is held at the target site for therapeutic agent delivery for a duration of not more than about 5 minutes, preferably not more than about 2 minutes, and more preferably not more than about 1 minute. Because the present invention makes use of concentration-driven molecular diffusion rather than pressure-driven convention for the delivery of therapeutic agents, it allows for low delivery pressures and durations not heretofore known in the art. The delivery techniques of the present invention thus minimize the risk of tissue damage, ischemia, etc., commonly associated with conventional localized delivery techniques.

With specific reference to FIG. 1, the delivery of a therapeutic agent to a target location is accomplished with the use of a medical device 100 comprising a catheter 110 having an expandable portion 120. The expandable portion 120 of the catheter 110 is optionally coated with a polymer for holding the therapeutic agent during delivery into the body. The polymer coating 130 is preferably capable of absorbing a substantial amount of drug solution. The polymer coating 130 is placed onto the expandable portion 120 by any suitable mean such as, for example, by immersion, spraying, or deposition by plasma or vapor deposition. The polymer is typically applied to a thickness of about 1 to 30 microns, preferably about 2 to 5 microns. Very thin polymer coatings, e.g., of about 0.2–0.3 microns and much thicker coatings, e.g., more than 30 microns, are also possible. It is also within the scope of the present invention to apply multiple layers of polymer coating onto the expandable portion 120 of catheter 110. Such multiple layers can be of the same or different polymer materials, and may perform different functions (e.g., for biocompatibility, to control drug release, etc.).

The polymer coating 130 comprises any polymeric material capable of absorbing or otherwise holding the therapeutic agent to be delivered. The polymeric material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylatic acids, polyglycolic acids, polycaprolactones, polyhydroxybutyrate valerates, polyacrylamides, polyethers, and mixtures and copolymers thereof. Coatings from polymer dispersions such as polyurethane dispersions (BAYHDROL, etc.) and acrylic latex dispersions are also within the scope of the present invention. Preferred polymers include polyacrylic acid as described in U.S. Pat. No. 5,091,205, the disclosure of which is incorporated herein by reference; and aqueous coating compositions comprising an aqueous dispersion or emulsion of a polymer having organic acid functional groups and a polyfunctional crosslinking agent having functional groups capable of reacting with organic acid groups, as described in U.S. Pat. No. 5,702,754, the disclosure of which is incorporated herein by reference.

Figure 2:
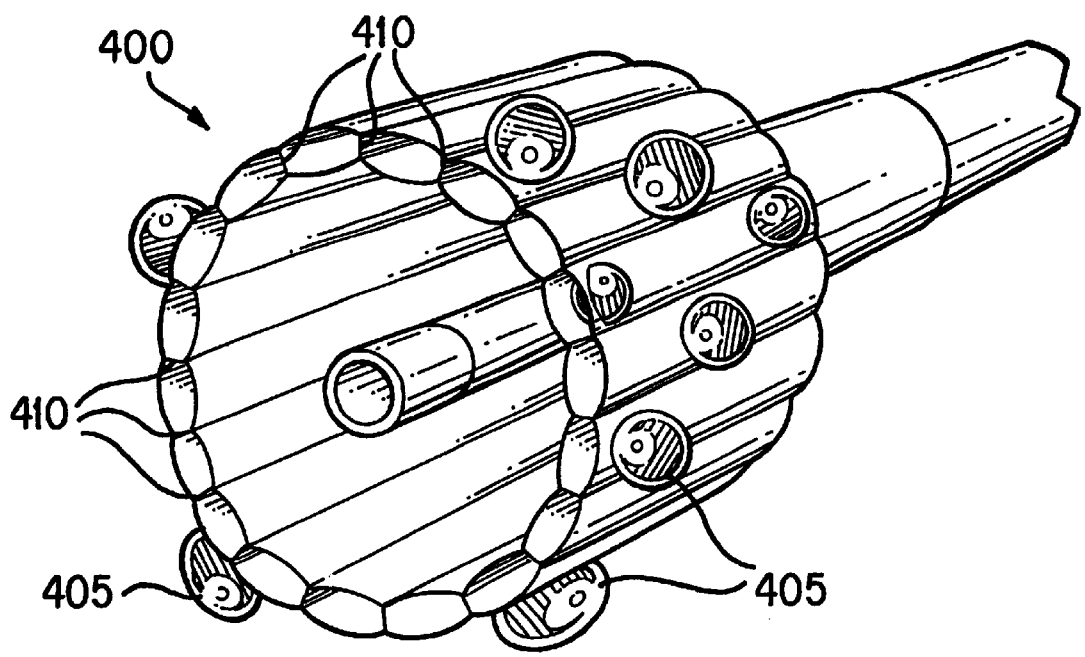
FIG. 2 shows a cross-section of an infusion catheter used in accordance with an embodiment of the present invention.

The therapeutic agent is introduced onto the expandable portion 120, or alternatively, into the polymer coating 130, by any suitable method. For example, the therapeutic agent is placed in solution, which is thereafter applied to the expandable portion 120 or polymer coating 130 by any suitable means, including dipping into the drug solution or applying the solution by pipet or spraying. In the former method, the amount of drug loading is controlled by regulating the time the polymer coating 130 is immersed in the drug solution, the extent of polymer coating cross-linking, the interactions between the polymer and drug (i.e., bonding, Van der Waals forces, charge interactions, etc.), the concentration of the drug in the solution and/or the amount of polymer coating 130. In another embodiment of the invention, the drug is incorporated directly into the polymer used in the polymer coating 130 prior to the application of the polymer as a coating onto a medical device. When the medical device used in the present invention is an infusion catheter 400, such as that shown in cross-section in FIG. 2, the substantially saturated solution of therapeutic agent (shown in FIG. 2 as 405) is not coated onto the catheter, but rather is delivered to the target tissue by infusing through the channels 410 of the infusion catheter 400.

The therapeutic agents used in the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, CDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, PPACK (dextrophenylalanine proline arginine chloromethylketone), rapamycin, probucol, and verapimil; angiogenic and anti-angiogenic agents; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. These and other compounds are added to the polymer coating using similar methods and routinely tested as set forth in the specification. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer coating 130, or whose DNA can be incorporated, include without limitation, angiogenic factors including acidic and basic fibroblast growth factors, vascular endothelial growth factor, epidermal growth factor, transforming growth factor α and β, platelet-derived enotheial growth factor, platelet-derived growth factor, tumor necrosis factor α, hepatocyte growth factor and insulin like growth factor; growth factors; cell cycle inhibitors including CDK inhibitors; thymidine kinase ("TK") and other agents useful for interfering with cell proliferation, including agents for treating malignancies; and combinations thereof. Still other useful factors, which can be provided as polypeptides or as DNA encoding these polypeptides, include monosite chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In one exemplary embodiment of the present invention, the medical device has recombinant nucleic acid incorporated therein, wherein the recombinant nucleic acid comprises a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u.") per milliliter ("ml"), preferably at least about $10^{11}$ p.f.u. per ml. Alternatively, the concentration of the viral vector is limited by the concentration that results in an undesirable immune response from a patient.

After the therapeutic agent is incorporated into the inflatable portion 120 or coating 130, the medical device 100 is introduced into the body and positioned to a target location through a body cavity or vasculature (e.g., coronary arteries, portal vein, ileofemoral vein, etc.) by torquing or other known techniques. Once the medical device 100 is positioned to a target location within the body, the expandable portion 120 is optionally expanded and the drug is released at a pressure of not more than about 5 atmospheres, preferably not more than about 1 atmosphere, and more preferably, not more than about 0.1 atmosphere. The medical device 100 is held at the target location for a duration of not more than about 5 minutes, preferably not more than about 2 minutes, and more preferably not more than about 1 minute. After delivery, the medical device 100 is removed from the body by known techniques.

Figure 3:
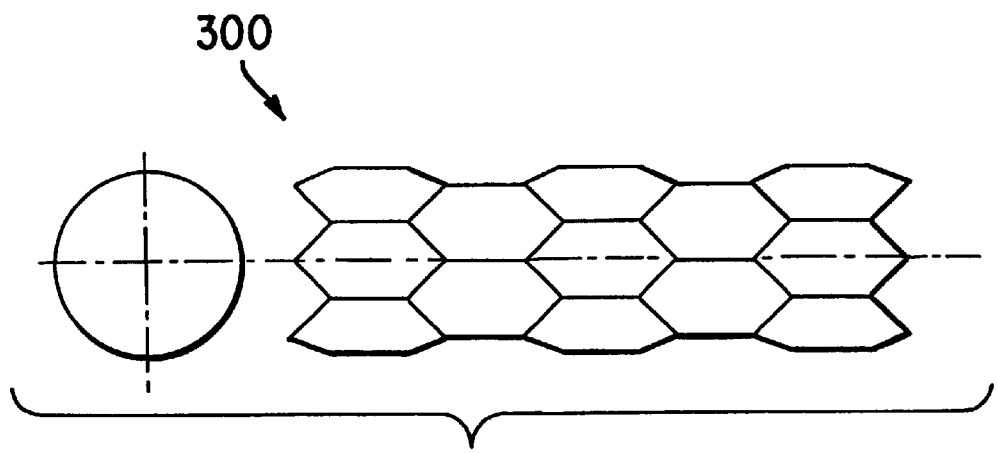
FIG. 3 shows a stent used in accordance with an embodiment of the present invention.

In one embodiment, the medical device 100 of the present invention includes a stent 300 (FIG. 3) for placement in a body lumen. The present invention can thus be used for the dual purpose of localized drug delivery and stent placement. As known in the art, stents are tubular support structures that are implanted inside tubular organs, blood vessels or other tubular body lumens. The stent used with the present invention is of any suitable design, and is either self-expanding or balloon-expandable. The stent is made of any suitable metallic (e.g., stainless steel, nitinol, tantalum, etc.), polymeric (e.g., polyethylene terephthalate, polyacetal, polylactic acid, polyethylene oxide-polybutylene terephthalate copolymer, etc.) or biodegradable material. The stent 300 is preferably metallic and configured in a mesh design, as shown in FIG. 3. When used with the present invention, the stent 300 is placed over the expandable portion 120 of the catheter 110.

The medical device 100 is thereafter delivered to a target location within the body. In this embodiment, the target location is situated within a body lumen. When the expandable portion 120 is expanded during the release of the drug agent from within the expandable portion 120 or the polymer coating 130, the stent 300 is likewise expanded. After the drug agent has been released from the expandable portion 120 or the polymer coating 130, the expandable portion 120 is compressed or deflated. The stent 300, however, remains in its expanded state within the body lumen.

Figure 4:
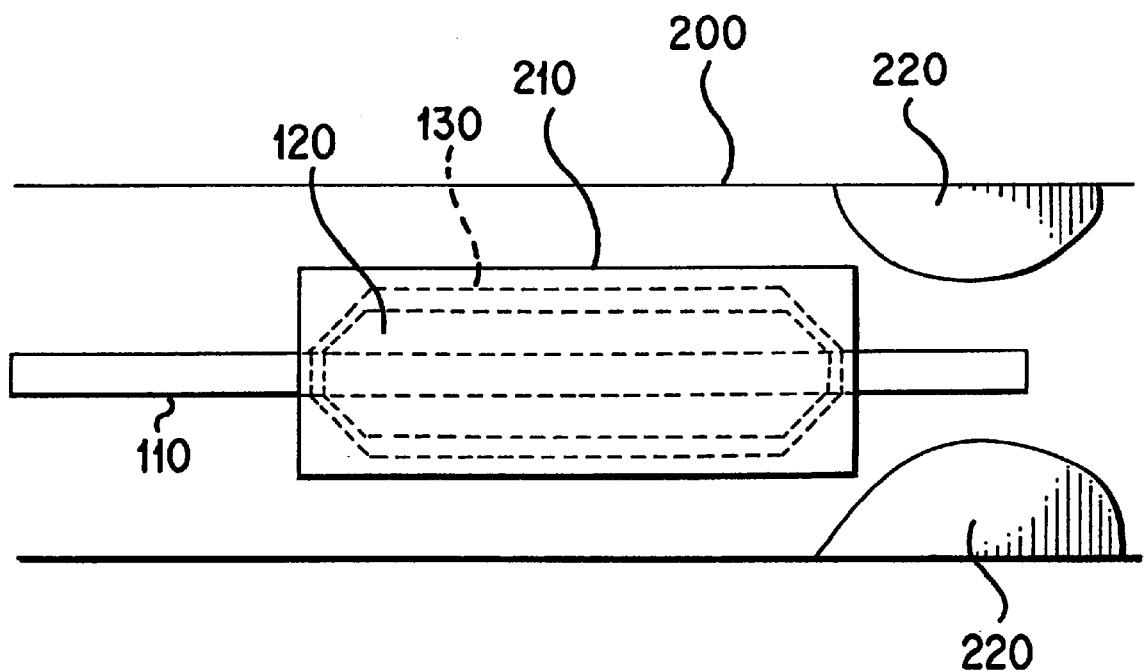
FIG. 4 shows a medical device being positioned to a target location within a body lumen, in accordance with an embodiment of the present invention.

Referring to the embodiment of the invention illustrated in FIG. 4, the expandable portion 120 of the catheter 110 is optionally covered by a protective sheath 210 while the medical device 100 is inserted into the body and positioned at a target location within a body lumen 200. Such a sheath is particularly advantageous in the case of long arterial transit times (i.e., to position the catheter to the target location) or when the therapeutic agent to be delivered is highly toxic. As the expandable portion 120 is positioned at a target occluded site 220, the protective sheath 210 is drawn back to expose the expandable portion 120 and thus to allow diffusion of the therapeutic agent into the target location 220. Alternatively, the sheath 210 remains stationary while the catheter 110 moves the expandable portion 120 forward into the occluded region. The sheath 210 protects the agent and coating 130, thus inhibiting premature release of the therapeutic agent.

In one embodiment, the medical device is a needle injection catheter rather than a balloon catheter. In this embodiment, the therapeutic agent is delivered to tissues atraumatically over a relatively short and clinically relevant time period, typically on the order of several seconds, by injecting a small volume (e.g., about 0.001 to about 1 ml) of a substantially saturated solution of therapeutic agent. Because the solution is substantially saturated, the concentration gradient of therapeutic agent resulting from injection drives the therapeutic agent deep into tissue by diffusion. Thus, in contrast to conventional local drug delivery techniques that make use of infusion pressure and volume to drive the drug deep into tissue, the method of the present invention achieves deep tissue penetration by a concentration driven mechanism. Consequently, the method of the present invention allows for the injection of therapeutic agent into tissues at low pressures, such as 1 atm or less, and with small volumes. One advantage of this embodiment over conventional techniques is that the low infusion pressure minimizes tissue damage, thus resulting in a potential increase in efficacy, transfection efficiency or the like.

Useful therapeutic applications to which the present invention can be applied include, without limitation, methods for treating, ameliorating, reducing and/or inhibiting any lumen or tissue injury, including those that result in denuding the interior wall of a lumen, namely its endothelial lining, including the lining of a blood vessel, urethra, lung, colon, urethra, biliary tree, esophagus, prostate, fallopian tubes, uterus, vascular graft, or the like. Such injuries result from disease, as in the case of atherosclerosis or urethal hyperplasia (strictures), and/or from mechanical injury from, for example, deployment of an endolumenal stent or a catheter-based device, including balloon angioplasty and related devices.

Vascular therapies that benefit using the methods disclosed herein include, without limitation, cardiomyopathies, cardiac and cerebral strokes, embolisms, aneurysms, atherosclerosis, and peripheral and cardiac ischemias. Delivery of genes encoding proteins competent to induce collateral blood vessel formation can be used to advantage in treating these disorders. Delivery of genes encoding proteins competent to interfere with neointimal (smooth muscle) cell proliferation also is particularly useful in treating restenosis.

Non-vascular therapies that benefit using the methods disclosed herein include urogential applications, including therapies for incontinence, kidney stones and the like. Here devices typically are implanted for a prescribed period of time and local delivery of genetic or chemical agents competent to induce an antibacterial, anti-inflammatory, or anti-encrustation effect are advantageous. In other applications, the delivery of anti-inflammatory agents, genetic or otherwise, is used to treat prostatitis, interstitial cystitis and other urogenital inflammatory disorders. Antiproliferative agents, genetic or otherwise, also can be used in endometriosis therapies. Still another application is in the delivery of anticancer agents, genetic or otherwise. The methods of the invention can be applied to therapies for bladder, prostate and uterine cancer. Similarly, delivery of agents to the interior of the lung to treat lung disorders, including cancers, cystic fibrosis and the like can be used to advantage.

The methods of the present invention can also be used to deliver diagnostic and/or imaging agents, including ultrasound contrasting agents such as perfluorocarbon. Other contrasting agents are well known to those skilled in the art. The contrasting agent is typically a microbubble encapsulated in a lipid, lipid-like or protein coat for catheter-based delivery. The microbubble further can have a tissue-targeting agent on its surface. Once delivered to the site of interest, the microbubble is burst or otherwise detected using ultrasound enhancement. The contrasting agent also can be combined with a therapeutic agent, genetic or otherwise, which then is delivered when the bubble is burst by ultrasound enhancement. Delivery to large surface areas such as lung and uterus interiors can benefit from this protocol.

Penetration enhancers are optionally used in any embodiment of the present invention. As is known in the art, penetration enhancers are substances or processes which facilitate the transport of solutes across biological membranes. When used in accordance with the present invention, penetration enhancers further increase the rate of penetration of therapeutic agents into tissues, thus allowing for more efficient drug transfer. Common classes of penetration enhancers include chelating agents such as EDTA, citric acid, salicylates, derivatives of collagen and diketones; surfactants such as SDS and polyoxyethylene-9-lauryl ether; non-surfactants such as cyclic ureas, 1-alkyl and 1-alkenylazacycloalkanone derivates; bile salts and derivates such as sodium deoxycholate, sodium, tauro-cholate, STDHF, and sodium glycodihydrofusidate; fatty acids and derivatives such as oleic acid, caprylic acid, capric acid, acylcarnitines, acylcholines, and mono and diglycerides; divalent and polyvalent cations; and enzymes such as elastase. Alternatively, a penetration enhancer used in conjunction with the present invention includes a process such as ultrasound, the application of an electric field, and/or other processes which increase the rate of penetration of therapeutic agents into tissues.

The invention is further described with reference to the following non-limiting examples.

EXAMPLES

All examples described herein were conducted for the in vivo delivery of an adenoviral trans-gene. The trans-gene used was recombinant nuclear specific β-galactosidase under the control of the cytomegalovirus promoter. Viral titer was measured by standard plaque assay using 293 cells. Viral solutions were thawed on ice and diluted with saline to appropriate concentrations. The viral solutions were used immediately after dilution.

New Zealand white rabbits (3.5–4.0 kg) were anesthetized with ketamine (10 mg/kg) and acepromazine (0.2 mg/kg) following predeitation with xylazine (2 mg/kg). The bilateral external iliac arteries were used for all experiments. A 5 French ("Fr.") introducer sheath was positioned in the right common carotid artery under surgical exposure. An angioplasty catheter was introduced via the introducer sheath to the lower abdominal aorta under fluoroscopic guidance. Angiography of the iliac arteries was performed using 2 ml of non-ionic contrast media. Rabbit weights were monitored and kept within 3.5 to 4.0 kg to insure a balloon to artery ratio of about 1.2:1. Arteries were denuded of endothelium by conducting a triple inflation injury prior to delivery. Injury was conducted using a 2.0 cm, 3.0 mm diameter balloon catheter introduced with a 0.014 inch guidewire via the right common carotid artery into either the right or left external iliac artery. The catheter was inflated to pressure with 50% dilution of contrast media at 6 atm, three times for one minute per inflation. After treatment of one iliac artery, the contralateral iliac artery was treated with a new balloon catheter.

Replication-deficient adenoviral vector gene delivery was accomplished in vivo with the use of both infusion style local delivery catheters and hydrogel coated angioplasty catheters. The infusion based devices were used to deliver viral particles to the vessel wall by pressure driven convection combined with concentration driven diffusion. Transmural hydraulic pressure was created at the vessel wall and modulated using these devices by infusion the viral solution under a known applied pressure. Two infusion devices were used to modulate pressure at a constant delivery time: the Channeled balloon catheter (Boston Scientific Corporation, Natick, Mass.) was used for low to moderate infusion pressures and the Transport catheter (Boston Scientific Corporation, Natick, Mass.) was used for high pressure infusions. Concentration was modulated at a constant infusion pressure of approximately 0.1 atm. Additionally, hydrogel coated angioplasty balloons were used to deliver virus to the vessel wall by a purely concentration driven diffusive mechanism. The hydrogel coated angioplasty balloons were coated with a crosslinked polyacrylic acid polymer.

Example 1
Delivery with a Channeled Balloon Catheter

Replication deficient adenoviral vector gene delivery was accomplished in vivo with the use of a channeled balloon catheter 2.0 cm in length and 3.0 mm in diameter. The catheter was introduced with a 0.014 inch guidewire via the right common carotid artery into either the right or left external iliac artery. The balloon was inflated to a nominal pressure of about 6 atm, whereupon gene delivery was accomplished at an infusion pressure of about 0.1 or 3 atm. Either of 3 ml, 500 microliters ("$\mu l$"), or 200 $\mu l$ of viral solution was infused through the infusion port of the catheter using a 1 ml or 5 ml syringe. Infusions of 3 ml were necessary to create higher infusion pressures. The solution was infused slowly over approximately 2 minutes while monitoring infusion pressure using an online pressure transducer. Balloons were deflated and removed after either 2 or 30 minutes had elapsed from the time of positioning the catheter at the target site.

Example 2
Delivery with a Transport Catheter

Viral solutions were infused locally at high pressure using the Transport catheter 2.0 cm in length and 3.0 mm in diameter. The catheter was introduced with a 0.014 inch guidewire via the right common carotid artery into either the right or left external iliac artery. The balloon was inflated to a nominal pressure of about 6 atm, whereupon gene delivery was accomplished at an infusion pressure of about 8 atm. Approximately 3 ml of viral solution was infused through the infusion port of the catheter using a 5 ml syringe. The solution was infused slowly over approximately 2 minutes while monitoring infusion pressure using an online pressure transducer. Balloons were deflated and removed after about 2 minutes.

Example 3
Delivery with a Hydrogel Coated Balloon Catheter

Virus was applied to the hydrogel coating of angioplasty balloons by slowly applying 25 $\mu l$ of a $1.7 \times 10^{11}$ pfu/ml adenoviral β-galactosidase stock solution (replication deficient adenovirus carrying the $E\ coli$ β-galactosidase gene) onto the coating using a micro-pipette. A 2.0 cm long, 3.0 mm diameter loaded hydrogel coated balloon catheter was placed within a protective sheath and inflated to 2 atm. The entire assembly was advanced over a 0.014 inch guidewire via the right common carotid artery to the bifurcation leading to the external iliacs. The balloon was then deflated and quickly advanced further to either the right or left external iliac artery. Viral delivery was allowed to occur for either 2 or 30 min.

Comparison of Examples 1 to 3

Three days after transfection, iliac arteries were harvested immediately after perfusion with heparinized 0.9% saline solution via the lower abdominal aorta. The harvested vessels were washed with cold phosphate-buffered saline (PBS), fixed in 1% paraformaldehyde for 10 min, washed in PBS post-fixation. β-galactosidase activity was assessed by incubating arteries in X-GAL chromogen overnight at 37° C. After staining, vessels were rinsed in PBS and post-fixed in 1% paraformaldehyde.

Vessels were opened longitudinally and photographed through a dissecting microscope for gross assessment. The dark blue staining sites were considered transfected regions. The target-zone, usually at or near the center of the delivery site, was cross-sectioned and subsequently processed for histologic analysis. Specimens were embedded in paraffin sectioned into 5 $\mu m$ sections and counter stained with hematoxylin and eosin. Slides were examined by light microscopy for expression of the LacZ transgene product, nuclear β-galactosidase, and were considered positive only when dark blue staining was observed. Transfection efficiency was determined by counting stained versus total medial nuclei in each arterial section.

Effect of Applied Pressure on Transfection

As shown in Table I, applied pressures of 3 and 8 atm did not significantly affect viral delivery from infusion-based devices. Transfection efficiency of a 3 ml viral solution was 2.30±0.64% when infused at approximately 3 atm and 1.05±0.21% when infused at an average pressure of 8 atm using Channeled and Transport catheters, respectively.

TABLE I

Influence of infusion volume and pressure on viral transfection efficiency.

| Device | infused conc. (pfu/ml) | viral dose (pfu) | infusion volume (ml) | infusion pressure (atm) | % transduction |
|---|---|---|---|---|---|
| hydrogel | N/A | $4.3 \times 10^9$ | N/A | N/A | $2.04 \pm 0.75$ |
| channel | $1.7 \times 10^9$ | $5.1 \times 10^9$ | 3 | 3 | $2.30 \pm 0.64$ |
| transport | $1.7 \times 10^9$ | $5.1 \times 10^9$ | 3 | 8 | $1.05 \pm 0.21$ | p = NS for all combinations

A comparable level of gene transfection, $2.04 \pm 0.75\%$, was achieved at zero hydraulic pressure (no infusion volume) when the virus was delivered passively from a hydrogel coated balloon, providing an indication that molecular diffusion rather than convection is the predominant mechanism for viral transport in the vessel wall. Viral infusion volume and pressure were determined not to have a statistically significant effect (p=not significant ("NS")) on transfection efficiency under each condition tested in Table I (all data were compared by a one-way analysis of variants).

Effect of Infusion Volume on Cellularity

Cellularity was assessed in 5 micron histological cross-sections by counting the number of nuclei stained by hematoxylin and eosin. Cellularity is expressed as the number of nuclei per cross-section. The higher volume deliveries, and consequently higher pressure infusions, from Channeled and Transport balloon catheters resulted in a significant loss of cellularity in the treated segment, as shown in Table II.

TABLE II

Influence of delivery parameters on cellularity.

| Device | infusion volume (ml) | infusion pressure (atm) | cellularity |
|---|---|---|---|
| none[1] | 0 | 0 | $845 \pm 34$ |
| hydrogel[2] | N/A | N/A | $833 \pm 17$ |
| channel[3] | 0.2 | 0.1 | $800 \pm 22$ |
| channel[4] | 0.5 | 0.1 | $863 \pm 24$ |
| channel[5] | 3 | 3 | $592 \pm 38$ |
| transport[6] | 3 | 8 | $600 \pm 34$ | p < 0.05 for 1, 2, 3, 4 versus 5, 6

Sections from these arteries demonstrated a reduction in medial smooth muscle cell number as indicated by a loss of visible cell nuclei for vessels treated with 3 ml of viral solution. In contrast, infusion volumes of 500 µl and less did not exhibit any observable detrimental effects on vessel wall cellularity.

Effect of Concentration on Transfection

The effect of an applied concentration on in vivo gene delivery was examined by delivering 500 µl of viral solution at three concentrations, $1.7 \times 10^{10}$, $5.6 \times 10^{10}$, and $1.7 \times 10^{11}$ pfu/ml, under an infusion pressure of 0.1 atm. Transfection increased by an order of magnitude from $1.8 \pm 0.4\%$ to $17.8 \pm 3.2\%$, in direct proportion to the increase in viral concentration from $1.7 \times 10^{13}$ to $1.7 \times 10^{11}$ pfu/ml. Such transfection levels are considered high for in-vivo β-galactosidase because of the presence of endogenous inhibitors. Histological staining of these arteries demonstrated a greater number of stained blue cells deeper into the media at the higher concentration of delivered virus relative to the lower concentration. Previous studies (Schulick et al., "In vivo Gene Transfer into Injured Carotid Arteries. Optimization and Evaluation of Acute Toxicity," 91 Circulation 2407–14 (1995)) have demonstrated a toxic response in the vessel wall when $1 \times 10^{10}$ pfu/ml of adenoviral β-galactosidase was delivered to rat carotid arteries. Here, the inventors have surprisingly shown that the channeled balloon catheter can be used to deliver viral solutions to rabbit iliac arteries at viral concentrations as high as $1.7 \times 10^{11}$ pfu/ml without an adverse effect on cellularity and with no observable inflammatory response.

Effect of Delivery Time on Transfection

The effect of delivery time on gene transfection was examined using hydrogel coated balloons. The balloons were left in contact with the vessel wall for either 2 or 30 minutes. As shown in Table III, transfection efficiency was $1.57 \pm 0.05\%$ and $2.04 \pm 75\%$ for delivery at 30 minutes and 2 minutes, respectively. In a related set of experiments, 200 µl of viral solution infused through a channeled balloon catheter over 2 minutes followed by no incubation or a 30 minute incubation where the balloon was left inflated. Transfection was $2.53 \pm 0.44$ and $2.00 \pm 0.52$ for delivery with or without a 30 minute incubation, respectively.

TABLE III

Influence of delivery and incubation time on viral transfection efficiency.

| Device | infused conc. (pfu/ml) | viral dose (pfu) | delivery time (min) | incubat. time (min) | % transduction |
|---|---|---|---|---|---|
| hydrogel[1] | N/A | $4.3 \times 10^9$ | 2 | 0 | $2.04 \pm 0.75$ |
| hydrogel[2] | N/A | $4.3 \times 10^9$ | 30 | 0 | $1.57 \pm 0.05$ |
| channel[3] | $26 \times 10^9$ | $5.1 \times 10^9$ | 2 | 0 | $2.52 \pm 0.44$ |
| channel[4] | $26 \times 10^9$ | $5.1 \times 10^9$ | 2 | 30 | $2.00 \pm 0.52$ | p = NS for 1 vs. 2 and 3 vs. 4

Example 4

In accordance with an embodiment of the present invention, heparin is locally delivered with the use of an infusion style balloon, such as in a channeled balloon catheter. A substantially saturated solution of heparin, having a concentration of about 1 gram per 20 ml of water, is infused at a target location for about 2 minutes at a pressure of about 0.1 atm. Using this approach, relatively small volumes of approximately 1 ml may be infused to achieve a therapeutic result, in comparison to the relatively higher volumes and pressures used in conventional techniques.

Example 5

In accordance with an embodiment of the present invention, verapamil is locally delivered with the use of an infusion style balloon, such as in a channeled balloon catheter. A substantially saturated solution of verapamil hydrochloride, having a concentration of about 62 mg/ml (i.e., about 75% of the solubility limit of 82 mg/ml for verapamil hydrochloride in water), is infused at a target location for about 2 minutes at a pressure of about 0.1 atm. Using this approach, relatively small volumes of approximately 1 ml may be infused to achieve a therapeutic result, in comparison to the relatively higher volumes and pressures used in conventional techniques.

Summary of Examples 1–5

By way of the present invention, a 2-minute clinically relevant delivery time was shown to be effective in achieving high levels of gene transfection in vivo. While prior studies have used delivery times greater than 20 minutes or an additional 30 minute incubation period post delivery from an infusion device such as a channel balloon catheter, the present inventors have shown that a 2 minute delivery time is at least or more effective than 30 minute delivery times. Since molecular diffusion is time-dependent, longer delivery times may have a positive effect under different conditions such as higher viral doses. In addition, a 30 minute incubation period post viral delivery from an infusion device, i.e. channel balloon catheter, was shown not to have a significant effect on gene expression. Thus, once the artery is reperfused and the concentration gradient is reversed, the virus does not back diffuse into the lumen. As the inventors have shown, long delivery times and extended incubation periods are not necessary for effective gene transfer once conditions have been optimized for a particular delivery device.

Example 6
Delivery with a Needle Injection Catheter

Recombinant replication deficient adenoviral particles encoding the gene for β galactosidase were injected into porcine myocardia using a needle injection catheter. A volume of 100 μl of viral solution was injected at a concentration of $1\times10^9$ pfu/ml and the results compared to those obtained using a 100 kl dose injection at $1\times10^{10}$ pfu/ml. Greater penetration of the virus was observed with the higher concentration injection, thus demonstrating greater diffusion of the virus due to the corresponding higher concentration gradient. Moreover, the higher concentration injection demonstrated greater transfection when compared to 250 μl injections at lower concentrations of $1\times10^9$ pfu/ml, thus demonstrating that high volumes are not necessary to achieve high degrees of transfection.

The inventors have demonstrated that viral particles penetrate arterial tissue in a manner analogous with a molecular diffusion mechanism. Consistent with this finding, the inventors have determined that concentration of therapeutic agent is the critical parameter for transport, and thus gene expression or therapeutic effect, in a vessel wall. The present invention is used to achieve significant transfection levels or therapeutic agent levels at a local site by delivering a small volume of concentrated therapeutic agent solution through a local delivery catheter at low pressure. Conversely, the inventors have determined that variations in applied pressure, which drives convective transport, does not significantly affect gene expression or drug delivery and/or uptake. Moreover, the inventors have found that gene expression occurs when a viral solution is delivered in a clinically relevant time frame of 2 minutes, thus indicating that longer times are not necessary to achieve efficient gene transfer.

What is claimed is:

1. A method of site-specifically delivering a therapeutic agent to a target location within a body cavity, vasculature, or tissue of a mammal, comprising the steps of:
    providing a catheter having a substantially saturated solution of therapeutic agent associated therewith, said therapeutic agent selected from the group consisting of pharmaceutically active molecules, proteins, and nucleic acids encoding an angiogenic factor,
    introducing said catheter into the body cavity, vasculature, or tissue;
    wherein a volume of said solution of therapeutic agent is released from said catheter at the target location at a pressure not more than about 0.1 atmospheres.

2. The method of claim 1, wherein said catheter is a channeled balloon catheter.

3. The method of claim 1, wherein said catheter is a transport catheter.

4. The method of claim 1, wherein said catheter is an infusion sleeve catheter.

5. The method of claim 1, wherein said catheter is balloon catheter having an expandable portion.

6. The method of claim 5, further comprising the steps of:
    coating said expandable portion with a polymer coating; and
    incorporating said therapeutic agent into said polymer coating.

7. The method of claim 6, wherein said coating comprises a polymer selected from the group consisting of polycarboxylic acids, cellulosic polymers, gelatin, polyvinylpyrolidone, maleic anhydnde polymers, polyamides, polyvinyl alcohols, polyethylene oxides, glycosamnoglycans, polysacchaxides, polyesters, polyuretbanes, silicones, polyorthoesters, polyanhydrides, polycarbonates, polypropylenes, polylactic acids, polyglycolic acids, polycaprolactones, polybydroxybutyrate valerates, polyacrylamides, polyethers, polyurethane dispersions, acrylic latex dispersions, polyacrylic acid, and mixtures and co-polymers thereof.

8. The method of claim 5, further comprising the steps of:
    placing a sheath over said expandable portion before said step of positioning said catheter to said target location; and
    removing said expandable portion from said sheath before said step of releasing said solution of therapeutic agent from said catheter.

9. The method of claim 1, wherein said catheter comprises a needle.

10. The method of claim 9, wherein said catheter is a needle injection catheter.

11. The method of claim 9, wherein said needle is a hypodermic needle.

12. A method of site-specifically delivering a therapeutic agent selected from the group consisting of therapeutically active molecules, protein and nucleic acids encoding an angiogenic factor to a target location within a body cavity or vasculature of a mammal, comprising the steps of:
    providing a catheter having a substantially saturated solution of therapeutic agent incorporated therein, said solution comprising a physiologically acceptable solvent and said therapeutic agent and wherein the concentration of said therapeutic agent in said solution is at least about 75% of the limit of solubility of said therapeutic agent in said solvent,
    introducing said catheter into the body cavity or vasculature;
    positioning said catheter to said target location;
    wherein said solution of therapeutic agent is released from said catheter at a pressure not more than about 0.1 atmospheres.

13. The method of claim 12, wherein said catheter is a channeled balloon catheter.

14. The method of claim 12, wherein said catheter is a transport catheter.

15. The method of claim 12, wherein said catheter is an infusion sleeve catheter.

16. The method of claim 12, wherein said catheter is a balloon catheter having an expandable portion.

17. The method of claim 16, further comprising the steps of,
    coating said expandable portion with a polymer coating; and
    incorporating said therapeutic agent into said polymer coating.

18. The method of claim 17, wherein said coating comprises a polymer selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, polyurethane dispersions, acrylic latex dispersions, polyacrylir acid, and mixtures and co-polymers thereof.

19. The method of claim 17, further comprising the steps of placing a sheath over said expandable portion before said step of positioning said catheter to said target location; and removing said expandable portion from said sheath before said step of releasing said solution of therapeutic agent from said catheter.

* * * * *

UNITED STATES PATENT AND TRADEMARK OFFICE
CERTIFICATE OF CORRECTION

PATENT NO.     : 6,369,039 B1
DATED          : April 9, 2002
INVENTOR(S)    : Palasis et al.

It is certified that error appears in the above-identified patent and that said Letters Patent is hereby corrected as shown below:

<u>Column 4,</u>
Line 4, "mean" should read -- means --.

<u>Column 5,</u>
Line 29, "anticodies" should read -- antibodies --; and
Line 42, "vascoactive" should read -- vasoactive --.

<u>Column 6,</u>
Line 1, "enotheial" should read -- endothelial --.

<u>Column 9,</u>
Line 34, "infusion the" should read -- infusion of the --.

<u>Column 11,</u>
Line 58, "1.7x1013" should read -- 1.7x1010 --.

<u>Column 12,</u>
Line 1, "1x1010" should read -- 1x1011 --.

<u>Column 13,</u>
Line 23, "100 kl" should read -- 100 μl --.

<u>Column 14,</u>
Line 13, "anhydnde" should read -- anhydride --;
Line 15, "glycosamnoglycans" should read -- glycosaminoglycans --;
Line 15, "polysacchaxides" should read -- polysaccharides --; and
Line 18, "polybydroxybutyrate" should read -- polyhydroxybutyrate --;

UNITED STATES PATENT AND TRADEMARK OFFICE
CERTIFICATE OF CORRECTION

PATENT NO.    : 6,369,039 B1
DATED         : April 9, 2002
INVENTOR(S)   : Palasis et al.

It is certified that error appears in the above-identified patent and that said Letters Patent is hereby corrected as shown below:

Column 15,
Line 11, "polyacrylir" should read -- polyacrylic --;

Signed and Sealed this

Twenty-eighth Day of January, 2003

JAMES E. ROGAN
*Director of the United States Patent and Trademark Office*